US00PP09884P

United States Patent [19]

Bessho et al.

[11] Patent Number: Plant 9,884

[45] Date of Patent: May 6, 1997

[54] PETUNIA PLANT NAMED 'LIRICASHOWER ROSE'

[75] Inventors: Masao Bessho; Seiji Nakamura, both of Kakegawa; Hitoshi Kojima, Kikukawa-machi, all of Japan

[73] Assignee: Sakata Seed Corporation, Yokohama, Japan

[21] Appl. No.: 585,850

[22] Filed: Jan. 16, 1996

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—James R. Cypher

[57] ABSTRACT

Disclosed herein is a new and distinct decumbent type Petunia plant named 'Liricashower Rose', having compact growth habit bred from crosses made in Japan from South America commercial Petunias of creeping growth habit. The new variety is strongly branching with a great profusion of blooms. The flowers are single and small with bright purplish rose colored petals. The plant is highly resistant to rain, heat, and drought.

2 Drawing Sheets

BACKGROUND

This invention relates to a new and distinct cultivar of Petunia plant, hereinafter referred to by the name 'Liricashower Rose'. 'Liricashower Rose' Petunia originated from a hybridization made in 1991 by the inventors Masao Bessho, Seiji Nakamura, Hitoshi Kojima at Sakatas Seed Corporation, Kakegawa breeding station in Kakegawa, Japan. The female parent was a bright purple red, creeping habit plant with breeder code 1C-1 and the male parent was a bright purple red, creeping habit plant with breeder code 3M-1. Both parents originated from the commercial markets in South America. The crosses (breeder code $F_1$) were pollinated in the early spring of 1992 to obtain breeder code $F_2$ seed. The resulting $F_2$ seeds were sown in the summer of 1992 for selection of better creeping and branching habit. Subsequent selected plants were maintained by vegetative propagation by cutting. The primary asexual propagation occurred in 1992. In 1993, cuttings from the plants were field grown for further selection of desired traits. Again in 1994, the cuttings of selected plants were field grown for final selection and evaluation for stability of desired traits. These asexual reproductions, of the final selection, by cuttings and field grown trial planting were performed at the Sakata Seed America, Inc. research station at Salinas, Calif., and the Sakata Seed Corporation breeding station in Kakegawa, Japan under the direction and supervision of the inventors. The invention, 'Liricashower Rose' Petunia, after three years of successive vegetative propagation by cuttings was determined by the inventors to have its combination of characteristics as herein described firmly fixed.

'Liricashower Rose' is a new variety of Petunia plant having a decumbent and compact habit. The plant has abundant branching and a large profusion of blooms and makes an excellent presentation in hanging baskets. The flowers are single, small in size (2.9 cm) and petals are a bright purplish rose color (R.H.S. 74A). The plant is highly resistant to rain, heat, and drought. The plant grows and flowers best under low soil pH conditions (5–6pH). Typcially, young flowers will close under low light and low temperature conditions such as conditions late in the day and at night.

The new cultivar is distinguished from any other Petunia plants of which we are aware by its purplish rose color, and excellent creeping-branching habit and large profusion of blooms making it a particularly desirable plant for hanging basket arrangements.

The closest commercial cultivar to my new variety of which I am aware is the Petunia plant named 'Milton Bell Pink'. The distinguishing characteristics which are outstanding in the new cultivar and which distinguish it from 'Milton Bell Pink' are:

| | 'Liricashower Rose' | 'Million Bell Pink' |
|---|---|---|
| Habit | Creeping Vigorous Growth | Erect Compact Growth |
| Flower Size | 2.9 cm | Smaller |
| Flower Color | Bright Purple Rose Lighter than 'Million Bell Pink' | Bright Purple Red |
| Flower Throat Color | Light Green Yellow | Bright Green Yellow |

BRIEF DESCRIPTION OF DRAWINGS

The accompanying drawings serve by color photographic means to illustrate the new plant variety, 'Liricashower Rose'. The colors are represented as true as possible using conventional photographic procedures.

1. full bloom with stem

2. bud with stem

3. small bud (unopened)

Figure 1:
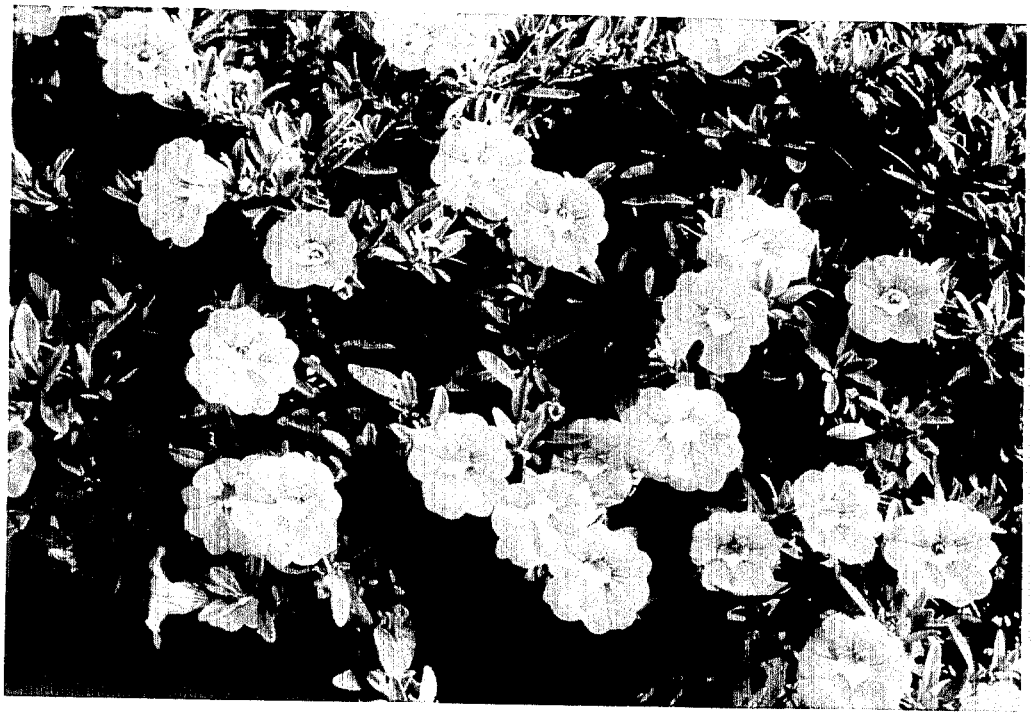
FIG. 1 is a close-up view of multiple blooms illustrating the decumbent, compact habit; abundant branching; and large profusion of blooms.
Figure 2:
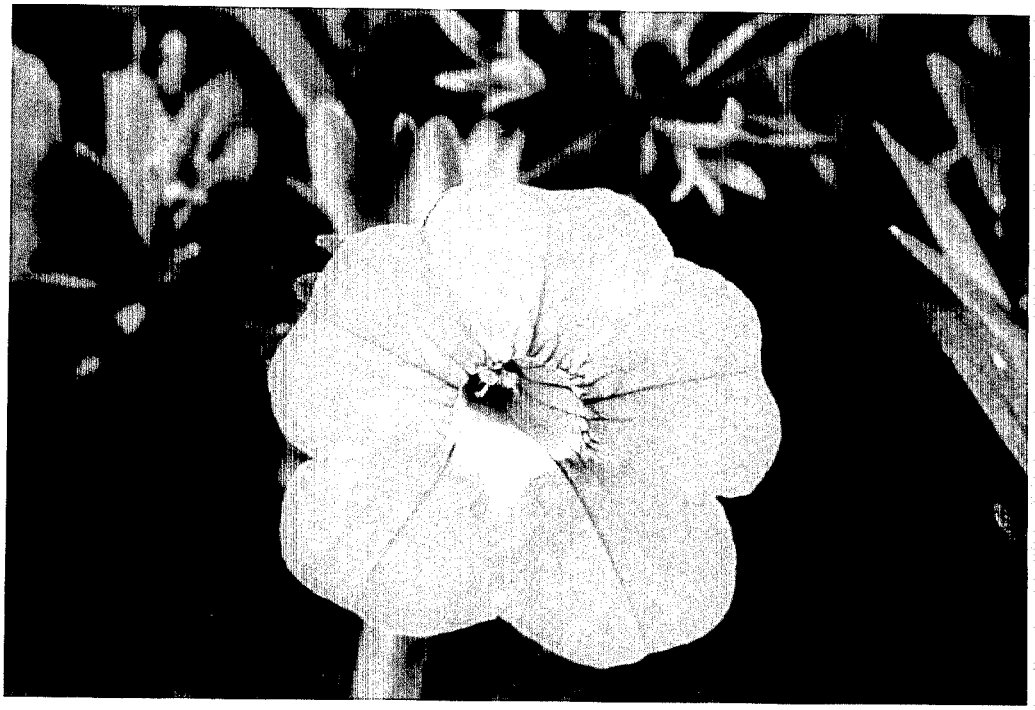
FIG. 2 is a close-up view of a single bloom.
Figure 3:
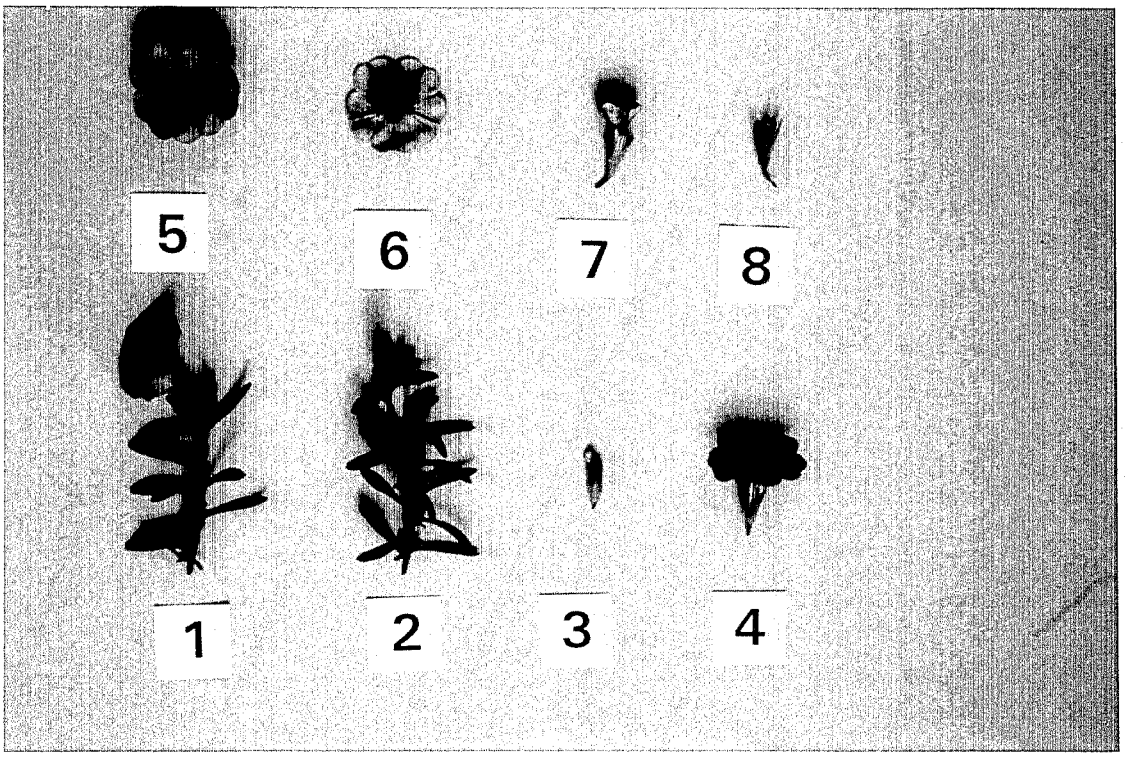
FIG. 3 is a view of the new cultivar in various stages of flower development.

4. side view of flower in full bloom

5. front view of the flower in full bloom

6. rear view of flower in full bloom

7. side view of partially opened flower

8. pistil and stamens of full bloom flower stage

DETAILED DESCRIPTION OF THE NEW VARIETY

The following description is based on observations and measurements of pot grown plants in Salinas, Calif. Color designations were made according to The Royal Horticultural Society Colour Chart published by The Royal Horticultural Society of London, England.

PLANT

Origin: Seedling

Parentage:

*Female parent.*—Unpatented and unnamed commerical market plant from South America, breeder Code 1C-1.

*Male parent.*—Unpatented and unnamed commercial market plant from South America, breeder code 3M-1.

Classification:

*Family.*—Solanaceae.

*Genius.*—Petunia.

*Botanical.*—Unknown; Petunia species.

*Commercial.*—Petunia 'Liricashower Rose'.

Growth habit: Decumbent.

Plant height: 5–7 cm, will mound on itself.

Spreading area of the plant: Stems extend to a length of 40–50 cm for a spreading area of 80–100 cm (in a 4 inch pot).

Growth: Vigorous growth with excellent basal branching and a profusion of continuous flowers.

Blooming period: Continuously under moderate temperatures of 15–25 degrees centigrade.

Resistance: Excellent resistance to rain, heat and drought.

Stem:

*Thickness.*—Main stem 2–2.5 mm; laterals 1–1.5 mm.

*Color.*—Yellowish green R.H.S. 143B with anthocyanin present on the axial portion of the stem.

*Pubescence.*—Slight.

*Branching.*—Abundant.

*Length of internode.*—4 mm at base of stem to 2 cm near tips of stems dependent on growing temperature.

Leaf:

*Phyllotaxis.*—Verticillate.

*Leaf attaching angle.*—Primarily vertical.

*Shape.*—Slightly oblanceolate and entire.

*Shape of tip.*—Acute.

*Size(average).*—9 mm long and 2 mm wide on smallest leaf in the whorl, 2.5 cm long and 6 mm wide on largest in the whorl.

*Thickness.*—0.5 mm–0.8 mm.

*Color.*—Grayish green R.H.S. 137B.

*Pubescence.*—Slight.

Flowers:

*Quantity.*—Abundant.

*Type.*—Opens obliquely upward, single.

*Shape.*—Funnel shape, with 5 fissured limb, a gamopetalous corolla, slight indent on each petal.

*Shape of tip.*—Retuse.

*Lobation.*—None.

*Undulation of margin.*—None.

*Diameter.*—2.5 cm–2.9 cm when fully open.

*Color.*—Unopened stage: grayish lavender R.H.S. 97B with dark venation on upper 3 petals, no venation on the lower 2 petals.

*Full bloom.*—Opened; bright purplish ose R.H.S. 74A and fading slightly with age to 74B, throat, white on lower portion to pale cream to light green yellow tones on upper portion.

*Reproductive organs.*—One pistil, five stamens, 2 with long filaments bending upward over the pistil and 3 short filaments, anther is yellow, filaments are white.

*Peduncle.*—Length is 1.5 mm on fully opened flowers, 0.6 mm on young flowers.

We claim:

1. A new and distinct cultivar of Petunia plant named 'Liricashower Rose', as herein illustrated and described.

* * * * *